United States Patent [19]

Gildenberg

[11] 4,037,585
[45] July 26, 1977

[54] METHOD OF MEASURING BLOOD FLOW BY RADIATION

[76] Inventor: Philip L. Gildenberg, 6218 Claridge, Houston, Tex. 77035

[21] Appl. No.: 621,539

[22] Filed: Oct. 10, 1975

[51] Int. Cl.² ............................................. A61B 6/02
[52] U.S. Cl. .................................................. 128/2 A
[58] Field of Search ......... 128/2 A, 2 R, 2 V, 2.06 F, 128/24 A; 250/362, 363–366, 369, 395, 358 P, 358 R

[56] References Cited

U.S. PATENT DOCUMENTS

| | | | |
|---|---|---|---|
| 3,670,715 | 6/1972 | Perlhou et al. | 128/2 A |
| 3,759,247 | 9/1973 | Doll et al. | 128/2.05 F |
| 3,769,966 | 11/1973 | Youdin et al. | 128/2.05 F |
| 3,778,614 | 12/1973 | Hounsfield | 250/363 |

*Primary Examiner*—William E. Kamm
*Attorney, Agent, or Firm*—Clarence A. O'Brien; Harvey B. Jacobson

[57] ABSTRACT

A method of measuring relative blood flow through at least a part of the body using penetrating radiation comprises transmitting a plurality of rays at an initial angle or initial mean angle through a planar slice of the body to define a first set of rays, transmitting a plurality of further sets of rays at angles or mean angles different from each other and from the initial angle or initial mean angle through the same planar slice of the body to define by the intersection of all such rays a two-dimensional matrix of elements of the body in the slice, measuring for each ray emerging from the body a number of momentary signals over the period of time at least equal to a pulse interval representing the momentary sum of the transmissions or absorptions of the element of the body intersected by the ray, determining from the momentary signals a difference signal representing the maximum difference between the momentary signals for each ray over the period of time, deriving sets of discrete difference signals corresponding to the sets of rays, the difference signals being indicative of the transmission or absorption of blood flowing through each element of the body in the matrix, and calculating from the difference signals resultant signals representing the transmissions or absorptions due to blood flow in the elements of the matrix. These resultant signals may be visually depicted on a cathode ray tube display, as a digital print-out, or as a photograph.

30 Claims, 8 Drawing Figures

METHOD OF MEASURING BLOOD FLOW BY RADIATION

The present invention relates to blood flow measurements in the head and other parts of the body and, more particularly, to a radiographic method of making such measurements.

The ability to measure local cerebral blood flow within the human brain in an important medical diagnostic tool which can be used to indicate the existence of or possibility of cerebral medical deficiences, e.g., arterial occlusion, arterial insufficiency and arterial and venous malformations. In addition, a knowledge of local cerebral blood flow permits differentation between types of tumors and the evaluation of whether or not the tumors are operable. While there are numerous diagostic techniques which permit a determination of total or gross regional blood flow, there are none which permit measurement of localized cerebral blood flow. Even those techniques that are known for measuring gross regional blood flow require the application of surgical techniques for the insertion of catheters or the ihalation or injection of radioisotopes. One exemplary technique is disclosed in U.S. Pat. No. 3,769,966 to Youdin et al which teaches a method for determining cerebral blood flow in discrete zones of the brain wherein the patient inhales a radioisotopic gas while wearing a headgear apparatus comprising about 144 radiation emission detectors arranged in a multiplanar array about the brain. One drawback to such techniquesis that they are sometimes attended by patient discomfort and/or the undesirability of administering radioactive materials internally. Further the measurement of gross regional blood flow is insufficient to accurately define blood flow patterns in the body.

It is therefore the primary object of the present invention to provide a method for measuring localized blood flow and defining blood flow patterns in the brain and other parts of the body.

It is another object of the invention to provide a blood flow measurement method which does not require the use of radioactive substances, surgical techniques or other procedures uncomfortable or potentially dangerous to the patient.

It is still another object of the invention to provide a method of blood flow which is rapid and accurate.

It is yet another object of the invention to provide a method of measuring both relative and/or absolute blood flow utilizing radiographic together with computer techniques.

It is another object of the invention to adapt and apply generally known automatic computerized transverse axial tomographic scanning techniques to the measurement of blood flow in the brain and other portions of the body.

Other objects and advantages will become apparent from the following description and appended claims.

Briefly stated, in accordance with the aforesaid objects, the present invention provides a method for measuring blood flow through the head, or other parts of the body, by passing a plurality of X or gamma ray collimated beams through a plurality of paths in a transverse section of the body in which flow is to be measured and detecting the pulsatile fluctuation of absorptions or transmissions in each path. From these pulsatile fluctuations, and employing generally known computer techniques, a visual display of relative blood flow patterns can be produced on an oscilloscope, as a contoured digital print-out, or as a picture or photograph.

The invention will be better understood from the following description considered together with the accompanying drawings, in which.

FIG,. 5 illustrates the wave form diagrams of an actual electrocardiogram signal of a human heart and the resulting pulsatile fluctuation of X-ray absorption signals due to blood flow through a cross-sectional slice of a patient's brain.

As is well known, automatic computerized transverse axial tomographic scanning is a radiological technique which permits the identification of tissue abnormalities through any transverse cross-section of the body by portraying in pictorial and/or quantitative form both the nature of the abnormality and its precise location in the body. The nature of the tissue abnormality is determined by means of its relative absorption coefficient for X or gamma rays and its location is ascertainable from the pictorial representation. Apparatus for practicing this radiological technique is presently available from a number of commercial sources, e.g., from Digital Information Science Corp., of Silver Spring, Maryland, and EMI Limited, of Hayes, Middlesex, England.

Although automatic computerized transverse axial tomographic scanning has been developed to the point where it can be employed to obtain information regarding any cross-section of the body using X or gamma radiation, it finds particular utility in examination and diagnosis of cerebral maladies. Therefore, for purposes of simplicity of description and ease of understanding, and without intending to be limited in application thereby, the known technique and the method of the present invention will be described herein in connectionwith their applicability to examinations of the head using X-radiation.

Figure 1:
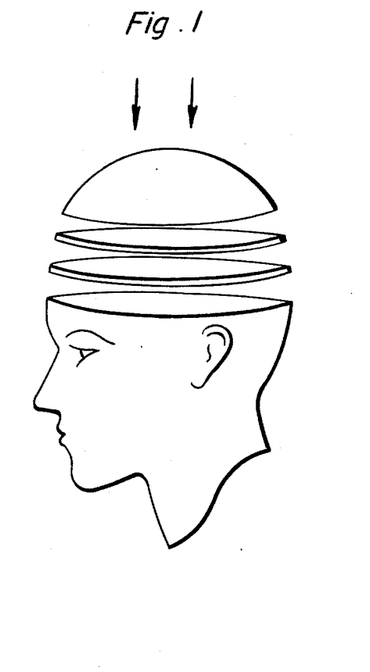
FIG. 1 illustrates typical transverse cross-sectional slices of the brain which can be examined by the present method.

In its simplest form, computerized X or gamma ray scanning of the brain is a new diagnostic method that utilizes modern electronic and computer technology for the measurement of the transmission of rays through tissue. The cranium is scanned in successive layers or slices by a narrow beam of rays in such a way that the transmission of the rays across a particular slice can be measured, and by means of suitable digital and analog computers, used to construct a detailed differential picture of the internal structure and tissues of the brain. FIG. 1 illustrates the nature of the series of thin, contiguous, cross-sectional slices which are typically examined by this technique. Each slice may be of any preselected thickness, but typically is in the range 3 to 6 millimeters thick. The resulting pictorial or digital representation of each slice is viewed as if the cranial contents are being looked at from above (see arrows in FIG. 1). The relative absorption coefficients of each point on the slice may be recorded on the visual representation of the slice by variations in color or shading or by actual digits in a digital print-out by the computer.

To understand how the scanning is accomplished, and why it is so accurate, it will useful to describe a typical procedure. The patient is placed in the prone or supine position on a table and the scanning apparatus is appropriately positioned with respect to the portion of the patient's head to be examined. The precise details of positioning the patient's head in the apparatus and the orientation of the apparatus are of no great import here and will vary depending upon the particular apparatus used. However, irrespective of the apparatus used, it should be appreciated that transverse axial tomography involves the production of X-ray absorption profiles made at a number of different angles by passing a series of highly collimated X-ray beams through the same transverse cross-sectional slice in the patient's head. Each collimted beam of X-rays passes through the head and is detected as it emerges, for example by a sodium iodide crystal. One reason for the great accuracy of this system is that the detectors enable the measurements of the relative absorption coefficients of the tissues to within ½%.

Figure 2:
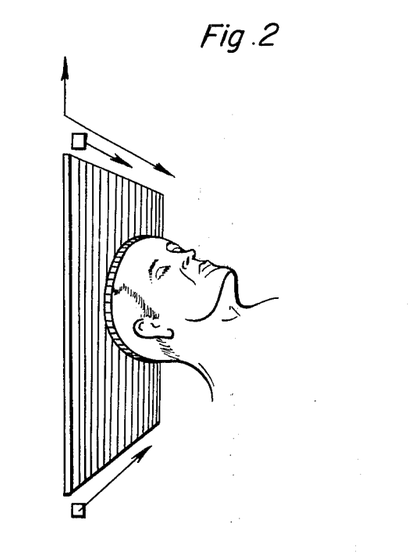
FIG. 2 illustrates a typical linear scan pass at a preselected angle through a cross-sectional slice of a patient's brain.
Figure 3:
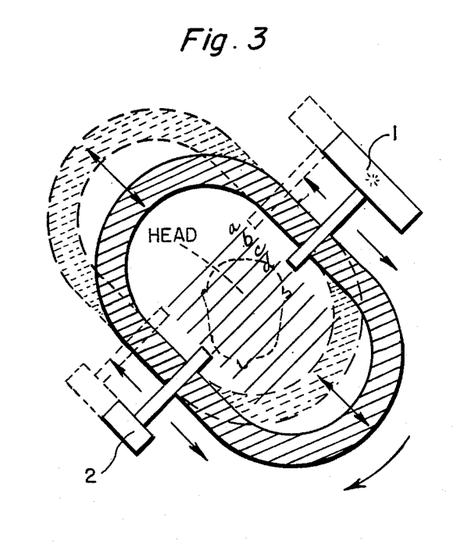
FIG. 3 illustrates the translational movement of the X-ray source and detector system during the linear scan pass shown in FIG. 2.
Figure 4:
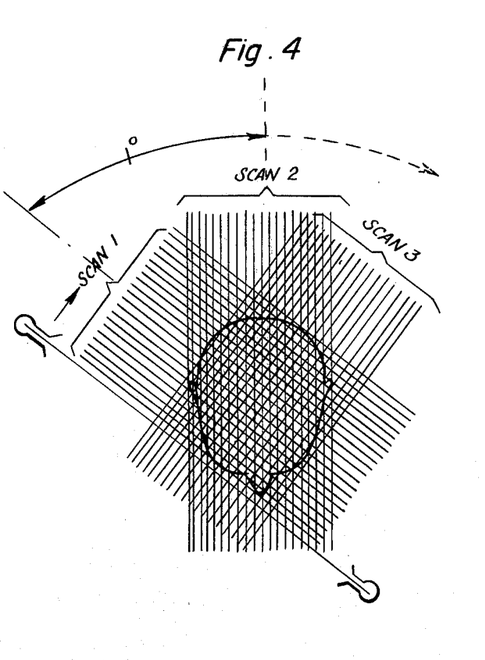
FIG. 4 illustrates a number of parallel beam scan passes, at different preselected angles, through the same cross-section of the patient's brain.

Referring to FIG. 2, the patient is shown supine on the table facing upwardly and is ready for examination. Each scan starts with a translational scan pass during which a parallel series of thin, collimated X-ray beams are passed through the pre-selected cross-sectional slice of interest at a pre-selected angle in the plane of the slice to produce a profile. As each beam transverses the head, some part of it is absorbed in the tissues through which it passes and the remainder is detected as it emerges. The absorption of each beam along any path depends on the sum of the absorption coefficients of the tissues through which the beam passes. A single X-ray profile, which may consist for example of about 160 parallel beams, is formed by linearly moving the X-ray source and detector system in such a manner that the source emits and the detector measures the intensity of each of the 160 emerging beams (see FIG. 3). The apparatus is then rotated in the plane of the cross-sectional slice (FIG. 4) and another scan pass is made at a new beam angle by again passing 160 parallel beams through the slice and measuring the emerging intensity of each beam to form another profile. This rotation of scanning is continued, typically at 1° intervals, so that a completed examination of a particular slice consists of a 180° rotation and 180 separate profiles. FIG. 4 illustrates for three scan passes how each point in the slice is scanned during each pass. Thus, after 180 passes of 160 beams each, it will be appreciated that every slice has been effectively subdivided into a matrix of elements. If the absorption coefficient of each element is considered as an unknown, and the X-ray source and emergence intensities are known, then the matrix of elements formed by the 160 beams in 180 passes defines about 28,800 separate elements or unknowns and at least an equivalent number of simultaneous equations.

The solution of such a series of simultaneous equations is a mathematical problem well within the capability of existing computer technology. See, for example, U.S. Pat. No. 3,778,614 to Hounsfield describing one method of solving just such a series by a process of successive approximations. The resulting solution, in the form of about 28,800 absorption coefficients can then be visually depicted as a matrix representation on an oscilloscope, television screen, photographic film, or as a digital print-out of calculated absorption coefficients presented in a matrix format that corresponds to the shape of the slice in the manner well known to the art and described in the aforementioned Hounsfield patent and in numerous publications, e.g., Ambrose, "Computerized X-Ray Scanning of the Brain", 40 J. Neurosurg. 679 (June, 1974).

Figure 5:
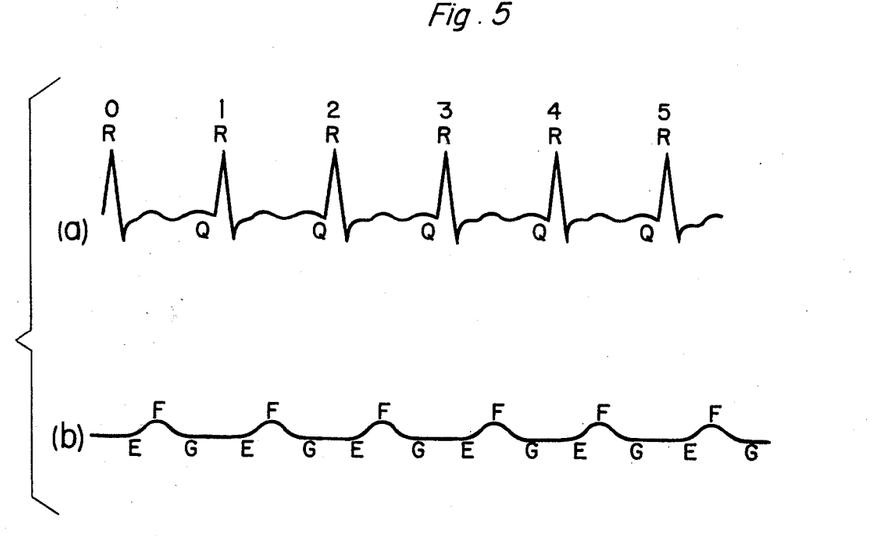

The present invention, of course, is not concerned with obtaining a visual representation of the absorption coefficients of all tissues present in each slice through which measurements are made. Rather, the instant invention seeks to obtain an indication of relative blood flow through any portion of interest in the head and to compare the flow with blood flow in another anatomically comparable portion of the head. The known technique for automatic computerized axial tomographic scanning cannot give any indication of blood flow through the head. Indeed, by its very nature, the known technique relies upon instantaneous measurements of X-ray beam intensities and, therefore, ignores blood flow through the tissues. As a matter of fact, the blood flow through, or more accurately the quantity of blood in, any part of the head is not constant with time. Rather, as is well known, blood flow is a pulsating phenomena and the quantity of blood present at any point in the head varies with cardiac contractions. Thus, following each cardiac contraction, there is a surge of blood through the head and, if any point in the head is monitored, it would be seen that the quantity of blood at that point will gradually increase to a maximum value shortly following cardiac contraction and then gradually drop off and that this cycle will repeat itself with each cardiac contraction. FIG. 5 graphically illustrates this phenomena wherein wave form (a) shows a series of reference electrocardiogram signals having the conventional wave form shape and being characterized by a spike at R representing the electrical activity of the heart muscles associated with the contraction of the ventricle, which causes the pulsatile surge of blood flow into the blood vessels leading to various parts of the body, including the head. Wave form (b) shows how blood flow at any point in the head is influencedby cardiac contraction, it being noteworthy that the blood flow peak F lags electrocardiogram spike R for each contraction.

Since the instantaneous measurements of X-ray transmission or absorption made by the known technique herein described of automatic computerized axial tomographic scanning are influenced by all matter, i.e. tissue, bone, blood, etc. in the slice through which the X-ray beam passes, to a certain extent each individual measurement reflects the absorption due to the presence of blood in the slice. However, the absorption due to the presence of blood may be a relatively small portion of the measured signal and, since the individual beam measurements are made randomly throughout the pulse period, and since multiple measurements of each element in the matrix are made, the pulsatile fluctuations in measurements due to absorption of X-rays in blood are averaged out in the final calculations. Thus, in effect, the fact of blood flow in the slice under investigation is ignored.

However, the present invention, which has as its object to measure relative blood flow at each point in the slice, obviously cannot ignore blood flow. Indeed, the present method essentially ignores the absolute coefficient of absorption of tissue and concentrates only on the very small pulsatile fluctuations in X-ray absorptions due to blood flow. In its broad embodiment, the present invention measures blood flow through the head, or other portions of the body, by measuring the fluctuation of X-ray transmission over the duration of a single pulse beat and uses this fluctuation to calculate the relative abosorption coefficients in the slice under investigation. Since the only matter through which the beam passes which can cause the value of the X-ray transmissions to vary is the relative amount of blood flowing through each element of the slice during the pulse beat, when only the pulsatile fluctuations are used to calculate absorption coefficients, the calculated coefficients are indicative of the quantity of blood passing through each element of the slice. When the calculated absorption coeffcients are visually depicted in the conventional manner, the resulting pictorial representation illustrates blood flow patterns in the slice. Moreover, the calculated absorption coefficients can be used to determine the absolute value of blood flow in each element of the slice in terms such as volume flow of blood per 100 grams of brain tissue per minute.

The present method will be better understood in its many embodiments from the following detailed description of its practice.

Figure 6:
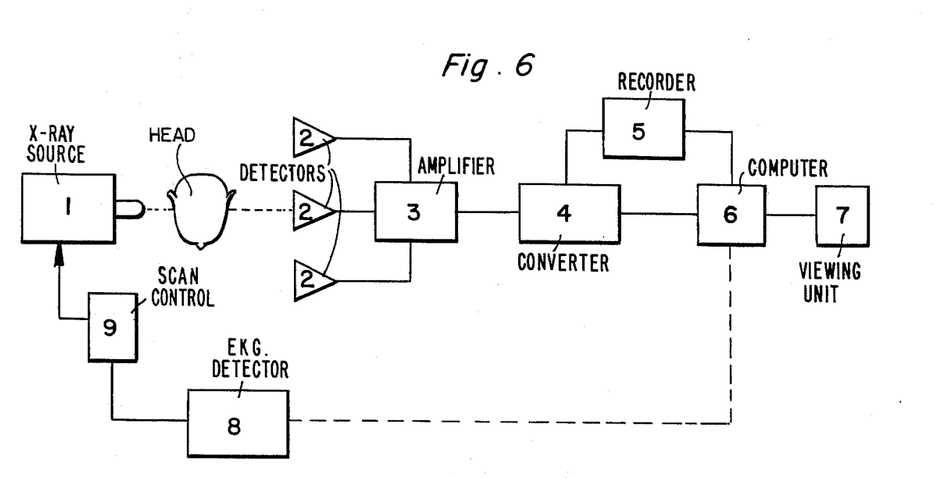
FIG. 6 is a block diagram of apparatus suitable for carrying out the method of the present invention.

With reference to FIG. 6, which shows in block form the apparatus useful in the present invention, the X-ray source 1 provides a highly collimated X-ray beam of small cross-section, e.g., 3 millimeters in maximum dimension, which, after passage through the head, is detected by at least one detector 2 and preferably by a plurality of detectors, as will be more fully explained hereinafter. Detector 2 may be a scintillation detector with scintillation counter or other type of detector which can accurately measure the moment to moment fluctuation in transmitted radiation. The detector receives and measures the intensity of the collimated beam emerging from the patent's head. Just as with automatic computerized axial tomographic scanning, for example as illustrated in FIGS. 1 through 4, the head is scanned in thin, continguous successive slices. However, instead of a smooth continuous scan pass of 160 beams yielding a profile, each scan pass according to the present invention must be interrupted continuous, i.e., the aligned source 1 and detector 2 must pause for each beam for a period of time equal to at least a pulse interval, which may be less than one full pulse cycle, but which is at least the period of time necessary to detect the maximum and minimum X-ray intensities during the pulse cycle. During each pause, the detector continuously measures the X-ray beam intensity which fluctuates as the quantity of blood present in the elements through which the beam is passing varies. Of interest in the present invention are the maximum and minimum values of X-ray beam intensity during the pulse cycle and particularly their difference, which difference is utilized in the subsequent calculations. Following the pause, the aligned source and detector move to the next point in the scan pass (e.g., from (a) to (b) in FIG. 3) at which point the apparatus pauses for at least a pulse interval, as hereinbefore defined, to permit detection of the maximum and minimum X-ray intensities during the pulse cycle. Movement of the apparatus continues along the scan path to points (c), (d), etc., with the apparatus pausing at each point for at least one pulse interval. Because of the need for intermittent pauses and to measure the maximum and minimum intensities in each pulse cycle, it will be appreciated that if a single source and detector are used, and if an effort is made to take 160 readings during each scan pass, even at a pulse rate of 80 pulses per minute, it would require two full minutes for each scan. If a full scan were made at each 1° angle through an arc of 180° as with automatic computerized axial tomographic scanning, a complete set of measurements would require 360 minutes or six hours, an impractically long period of time for a patient to be kept still. Fortunately, unlike scanning to obtain a complete tissue picture through each slice, blood flow measurement does not require that the matrix elements be quite as small and therefore fewer measurements can be used. It is believed that the minimum practical application of the present method requires five to eight readings (beams) per scan, although more accurate blood flow measurements will be obtained if more readings per scan are used. To accomplish a large number of readings in each scan within a practical period of time, it is only necessary to utilize a plurality of sources and detectors or a plurality of detectors with a single radiant source. Thus, in one embodiment, a gantry consisting of a series of 15 to 20 sources and detectors can be employed to simultaneously pass 15 to 20 X-ray beams through a single slice of the patient's head for a full pulse cycle. Following each pulse cycle, the gantry may be rotated through each portion of the predetermined arc, for example 1° of a 180° arc. In this manner, a complete examination of a slice, consisting of 15 to 20 readings per scan and 180 scans, can be completed in two to three minutes. Alternatively, some lesser number of sources and detectors can be employed, for example five to eight on a gantry, and the gantry moved in a linear scan pass as shown in FIG. 3 to three or four positions before each rotation. In this manner, each scan will consist of 15 to 32 readings and a complete examination, consisting of 15 to 32 readings per scan and 180 scans, can be completed in about 7 to 12 minutes. Although the examination time is a bit longer than where 15 to 20 sources and detectors are used, there is a considerable saving in terms of expense of the apparatus. From the foregoing, it will be appreciated that, in theory, as many or as few sources and detectors can be used as desired and, therefore, each scan pass can consist of as few as five to eight beams or as many beams as may be desired. Likewise, each complete examination can consist of measurements at 1° intervals along a 180° arc or of larger intervals, for example measurements at 2° or 3° intervals. Alternatively, a smaller arc may be employed, for example 90° to 180°. The type of examination necessitated by the medical condition of the patient will in most cases determine the number of readings per scan and the number of scans, and therefore the length and accuracy of the examination. Moreover, by appropriate apparatus design, more than one cross-sectional slice of the head can be examined during each scan pass. Therefore, it should be clear that the time to complete and the accuracy of the measurements which can be accomplished by the present method are limited only by apparatus design, which itself is a function of economics, and which is well within the technical skill of the art. The only limitation imposed on the method is that sufficient readings be made during an examination to permit substantial discrimination between the transmission or absorption coefficients due to blood flow through neighboring elements of the matrix.

However, irrespective of the number of beams employed per scan or the number of scans per examination, the essentials of the present method remain the same. Therefore, returning to FIG. 6, it will be seen that each detected momentary X-ray intensity measurement during a pulse interval is transmitted by the detector 2 as an electrical signal having a strength proportional to the beam intensity through an amplifier 3 to an analog to digital converter 4. In the converter, the electrical signal strength is converted to a number with which digital computer 6 can work. For each pulse interval, the computer identifies the maximum and minimum values of X-ray beam intensity, calculates their difference, and discards the other signals it received during the pulse interval. Alternatively, in lieu of discarding the other signals, if desired they can be used in the known technique of computerized axial tomography, for example as disclosed in U. S. Pat. No. 3,778,614, to produce a cross-sectional representation of the tissue of the head. This difference may be enhanced by introduction into the blood stream of a substance with a coefficient of absorption different from that of other body tissues, such as certain radio-opaque contract materials, certain plasma expanders such as Dexran, or certain iodinated compounds. A recorder 5 is optionally interposed between the converter 4 and digital computer 6 whereby the signals can be recorded and stored for future use, if desired. If a plurality of detectors 2 are used, the detected X-ray beam intensities are each separately amplified and converted and are individually received by the computer in such a manner that the computer can separately utilize each input signal.

The computer 6 accumulates all of the data fed to it in this manner for each beam of each scan and for each scan angle through each slice. The passage of $x$ beams per scan and the use of $y$ scans defines $xy$ elements per slice. As with automatic computerized axial tomographic scanning, each element represents an unknown; however, in the present method, the unknown is the fluctuation in X-ray absorption due only to blood flowing through the element. The resulting mathematical picture is a series of $xy$ simultaneous equations in $xy$ unknowns which can readily be solved by existing computer technology to ascertain the absorption in each element of the slice. The calculational technique employed to solve these equations is not a part of the present invention and may be any technique now known or which may hereafter become available. One suitable technique is explained in U.S. Pat. No. 3,778,614.

The solution to the equations, the absorption in each element of a slice, is passed to viewing unit 7 which may be, for example, a cathode ray oscilloscope, a color or black and white television screen, a teletype, or a digital line printer. The type of viewing unit employed may vary from patient to patient depending upon the diagnostic need. For example, if a black and white television screen is used, the different absorptions of each element are displayed as variations in shading from black to white to complete the picture. If a color television screen is used, a finite number of colors are used and each represents a range of absorptions whereby a complete picture of the slice can be portrayed. If a digital print-out is employed, each digit is the calculated absorption coefficient of blood at that point in the slice.

Irrespective of the display technique chosen, it will be appreciated that the absolute value of blood absorptions will vary considerably from point to point in the head. Thus, for example, where major blood vessels are present, the flow and corresponding pulsatile fluctuation absorption will be quite large compared to primarily tissue areas where there is only capillary blood flow. Since the display unit is arranged to respond to the output signals of the digital computer to build up a visual representation of the slice under examination, if, for example, a black and white display screen is used, the full scale of black to white will generally represent the entire range of pulsatile fluctuations in absorption coefficients. This is known as a broad contrast window. However, if it is desired to focus in on particular anatomical areas, for example a major blood vessel, it is possible to apply the full scale of black to white to represent only the limited range of pulsatile fluctuations in absorption coefficients applicable to the anatomical area of interest. This is known as a narrow contrast window. In this manner, the resulting pictorial display will have greater contrast within the area of interest and will permit distinguishing only small variations in blood flow which might otherwise have appeared as indistinguishable shades of gray if a broad contrast window had been used.

Since an essential feature of the present method is the use of interrupted continuous scanning and the detection of X-ray intensities over the period of at least a pulse interval, the linear movement of the scanning gantry and/or the rotation of the gantry must be coordinated with the pulse cycle. There are numerous ways to do this. One advantageous method involves simultaneously measuring the electrocardiogram of the patient and using that measurement to control the pauses and movements of the gantry. For example, referring to FIG. 5, as hereinbefore indicated, FIGS. 5(a) illustrates a typical electrocardiogram wave form and FIG. 5(b) illustrates the fluctuation of blood flow through the head with time relative to cardiac contraction. The important consideration in the X-ray intensity measurements is to assure that the entire blood flow wave form due to each cardiac contraction is measured in such a way that the maximum pulsatile fluctuation can be calculated. Thus, it may be necessary that the gantry be stationary at least for a period encompassing EFG in FIG. 5(b). It is desirable that the gantry move during the blood flow period GE and thereby be in its next measuring position in time to detect the very next EFG blood pulse. Thus it is a relatively simple matter to program the electrocardiogram detector 8 in FIG. 6 to signal the gantry scan or rotation control unit 9 at a preselected point in the electrocardiogram wave form, e.g., at Q in FIG. 5(a) corresponding to a time just following G in the blood pulse wave form EFG. At the same time, detector 8 signals the digital computer 6 that a pulse cycle has been completed, thereby actuating the computer to calculate the maximum difference in signal intensity received by it during the just completed pulse cycle and preparing the computer for the next set of signals representing measurements during the pulse cycle to follow. There are, of course, numerous other methods for initiating a signal upon the completion of a pulse cycle which can be used equally effectively in the present method, and it is not intended to limit the method to any particular means for signalling gantry movement.

Figure 7:
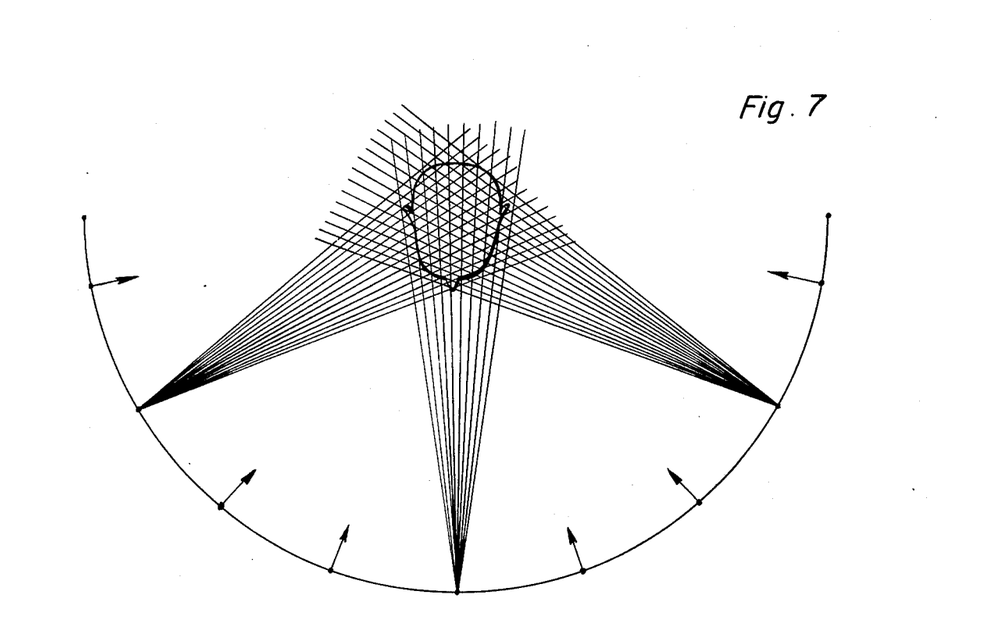
FIG. 7 illustrates a number of divergent beam scan passes through a single cross-section of a patient's brain resulting from rotating an X-ray source and aligned detectors in a preselected arc about the patient's brain.

It should be understood that the foregoing description of an operative and preferred form of the invention is not the only method of practicing the invention and numerous modifications can be made without actually departing from the essence of the invention. Thus, as already indicated, the method of coordinating gantry movement with the pulse cycle is not critical to the invention. Moreover, it is not necessary that the beams in each scan pass, as illustrated in FIGS. 2, 3 and 4, be parallel. Instead, a source of X-rays can be employed which emits a pie-shaped array of diverging beams, i.e., a series of beams diverging from a point in the outline of the sector of a circle. Thus, in one embodiment of the invention a single source can provide a series of diverging beams which pass through the patient's head and are detected by a plurality of detectors in the manner previously described herein. Each array of divergent beams can comprise a single scan and the source and detectors can rotate through a predetermined arc at predetermined arc intervals to define a matrix of elements in a single slice through the head. FIG. 7 illustrates just such an arrangement wherein the various arc intervals may be 1° or some other interval and the predetermined arc may be 180° or some other selected arc. It is noteworthy that although the divergent beams in each scan are at various angles, a mean angle can be identified for each scan and the arc interval between scans represents intervals between these mean angles. In fact, an array of divergent beams pausing for a full pulse cycle and then rotating through a predetermined arc interval between mean angles is an extremely desirable method of measuring blood flow where a relatively small number of beams per scan are employed. Alternatively, the technique illustrated in FIG. 3 can be combined with the technique illustrated in FIG. 7, utilizing a point source of divergent beams originating successively at several points along a linear scan, to increase the speed and efficiency of the technique. Moreover, it will be appreciated that the calculation of blood flow in several slices simultaneously can be accomplished using a three dimensional array of multiple detectors, and possibly multiple sources.

Figure 8:
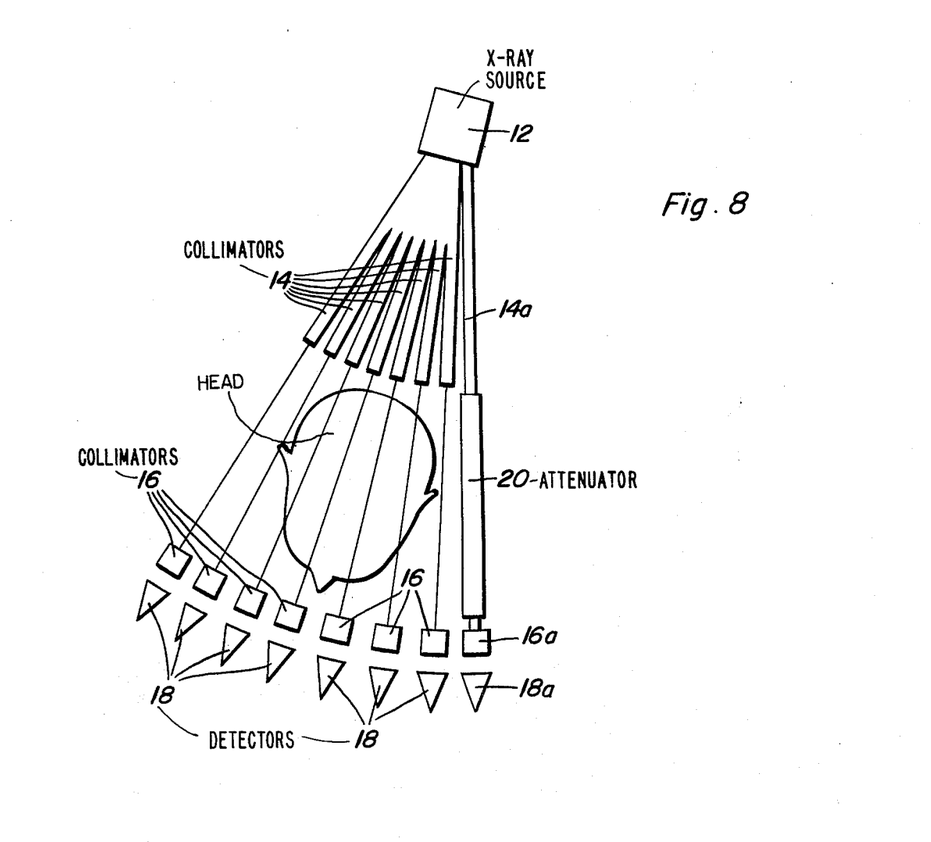
FIG. 8 illustrates schematically the scanning apparatus suitable for accomplishing the divergent beam scan-passes illustrated in FIG. 7.

The apparatus for accomplishing the scans shown in FIG. 7 is illustrated in FIG. 8. The X-ray source 12 emits a series of divergent beams which pass through collimators 14, through the cross-sectional slice under examination, through further collimators 16, and are detected by a series of scintillation detectors 18. A single one of the series of divergent beams passes through collimator 14a, through a dummy attenuator 20, through a further collimator 16a and is detected by reference scintillation detector 18a. The material of the attenuator 20 is selected to have similar absorption properties to the tissue in the slice under examination. The purpose of the reference detectors 18a and collimators 14a and 16a associated therewith is to assure consistent X-ray transmission readings independent of any variations in X-ray source intensity. Thus, for any given source intensity, the detector 18a measurement is known and any variation in this measurement can be used to adjust the measurements of the other detectors 18 to a standard X-ray source base.

In still another variation of the invention, where it is desired to examine only a small area within the head rather than the entire head, a single source and detector may be employed and a circular scan accomplished using scanning movements similar to those explained in connection with FIG. 5 of U.S. Pat. No. 3,778,614. Of course, in the present method, each beam must be detected for a period of at least one pulse cycle and the difference between the maximum and minimum X-ray beam intensities employed in the subsequent calculations. This scanning technique has the advantage that the elements of the matrix at the area of interest are relatively small and therefore considerable accuracy in the area of interest is obtainable. At the same time, the scanning technique is relatively rapid.

The relative absorption coefficients calculated for each element of each slice under examination can be diagnostically used in a number of ways. For example, for examinations of the head, it is usually the case that the suspected cerebral malady, e.g., arterial insufficiency, is present in only one hemisphere. Therefore, each visual display of a cross-sectional slice may be used as its own control and each hemisphere can be compared with the other hemisphere either visually or via point-by-point comparison of a digital printout. In a related technique, the computer could be pre-programmed with data representing measurements made in corresponding slices taken from "normal" controls and the computer can visually display the "normal" area of interest adjacent the area of interest of the head under examination to permit a visual comparison. Alternatively, the computer can be asked to itself compare its calculated absorptions with predetermined "normal" absorptions and to identify areas of significant variation.

In still another application, the calculated relative absorption values can be used to determine absolute blood flow rates at any point in the brain in terms such as milliliters of blood per 100 grams of brain tissue per minute. One way to accomplish this is to employ known techniques for measuring total blood flow or gross regional blood flow, e.g., the use of an Anger camera or the method of U.S. Pat. No. 3,769,966, and to calibrate these known techniques against the calculated absorptions. With a knowledge of the grams of brain tissue represented by each matrix element and the specific gravity of the brain tissue, a digital value can be calculated from the calculated absorption coefficients which represents the average of the relative blood flow in all the measured elements. If it is assumed that this calculated average corresponds to the total or gross regional blood flow determined by one of the known techniques, the actual blood flow in each element of the matrix can be determined as a difference from the calculated average.

Whether the present method can be employed to determine absolute blood flow in each element of the matrix without calibration to tother techniques is not now known. This is because it is not now known whether in the cerebral circulation, under all conditions, blood flow returns to zero in all major blood vessels during diastole (i.e., the minimum figure for each pulsatile fluctuation) or whether there is still flow because of the elasticity of the vessels. If blood flow during diastole is zero or consistent enough to estimate in all patients, then the pulsatile blood flow determined by the present method can be added to the diastole value to determine absolute blood flow. On the other hand, if diastole flow is not predictable in all patients, it will be necessary to employ the hereindescribed calibration procedure on each patient for whom it is desirable to determine absolute blood flow.

While the present invention has been described with reference to particular embodiments thereof, it will be understood by those skilled in the art that numerous modifications can be made without actually departing from the scope of the invention. Accordingly, all modifications and equivalents may be resorted to which fall within the scope of the invention as claimed.

What is claimed as new is as follows:

1. A method of measuring relative blood flow through at least a part of the body using penetrating radiation, comprising the steps of:
   a. transmitting radiation from an external source through the body in a plurality of rays traversing a plurality of respective paths to establish a first set of rays in a planar slice of the body, the cross-sectional dimensions of each ray being small in relation to the dimensions of the body and each ray traversing the body for a period of time at least equal to a pulse interval;
   b. transmitting radiation from said external source in further sets of rays similar to said first set of rays;
   c. one of said sets being disposed in said planar slice at an initial angle or initial mean angle and the other of said sets of rays being disposed in said planar slice at angles or mean angles different from each other and from said initial angle or initial mean angle;
   d. the sets of rays being such that every element of a two-dimensional matrix of elements of the body in said planar slice is intersected by a group of said rays, the group of rays being different for the different elements of the matrix, each element of said matrix having dimensions of the order to magnitude of the cross-sectional dimensions of said rays;
   e. deriving from each ray emerging from the body over the period of time at least equal to a pulse interval a number of momentary output signals, each said signal representing the momentary sum of the transmissions or absorptions of the elements of the body intersected by the ray;
   f. determining from said momentary signals a difference signal representing the maximum difference between said momentary signals for each ray over said period of time;
   g. deriving sets of discrete difference signals corresponding to the sets of rays, said difference signals being indicative of the transmission or absorption of blood flowing through each element of said matrix, the number of difference signals being sufficient to determine substantial discrimination between the transmission or absorption coefficients due to blood flow through neighboring elements of the matrix;
   h. deriving from said difference signals resultant signals representing the transmissions or absorptions due to blood flow in the elements of said matrix; and
   i. producing in response to said resultant signals a representation of the transmissions or absorptions due to blood flow in said elements of the slice of the body.

2. A method according to claim 1 wherein step (a) is carried out by scanning said source linearly with respect to said body to establish the first set of rays traversing said body at the initial angle in the planar slice of said body, and step (b) is carried out by repeating said linear scanning of said source at a plurality of different angles around the plane, to establish the further sets of rays disposed at angles different from each other and from said initial angle.

3. A method according to claim 2 wherein said rays in each set of rays are simultaneously transmitted during a period of time at least equal to a pulse interval and each further set of rays is transmitted during a successive period of time at least equal to a pulse interval, no two sets of rays being transmitted during the same period of time.

4. A method according to claim 3 wherein an electrocardiogram signal from the body is continuously monitored and the transmission of each further set of rays is coordinated with the pulse cycle in response to said electrocardiogram signal.

5. A method according to claim 2 wherein the first ray in each set of rays is transmitted during a period of time at least equal to a pulse interval and each succeeding ray in each set of rays is transmitted individually during a subsequent period of time at least equal to a pulse interval, no two rays in a set being transmitted during the same period of time.

6. A method according to claim 5 wherein an electrocardiogram signal from the body is continuously monitored and each transmission of each ray is coordinated with said pulse cycle in response to said electrocardiogram signal.

7. A method according to claim 2 wherein each set of rays comprises a number of ray groups and said first ray group in each set of rays is transmitted during a period of time at least equal to a pulse interval and each succeeding ray group is transmitted during a subsequent period of time at least equal to a pulse interval, no two ray groups in a set being transmitted during the same period of time.

8. A method according to claim 7 wherein an electrocardiogram signal from the body is continuously monitored and the transmission of each ray group is coordinated with said pulse cycle in response to said electrocardiogram signal.

9. A method according to claim 1 wherein said rays in each set of rays are substantially parallel.

10. A method according to claim 1 wherein each set of rays comprises from 5 to 160 rays.

11. A method according to claim 1 wherein each set of rays comprises from 5 to 30 rays.

12. A method according to claim 1 wherein not more than 180 sets of rays are transmitted for each slice.

13. A method according to claim 12 wherein 60 to 90 sets of rays are transmitted for each slice.

14. A method according to claim 1 in which the steps of transmitting radiation through the body are carried out such that each set of rays is disposed along respective radii of a respective sector of a circle, the locus of the centers of said circles generating a circle or arc lying outside said body.

15. A method according to claim 14 wherein an electrocardiogram signal from the body is continuously monitored; wherein no two sets of rays are transmitted during the same time period; and wherein the transmission of each set of rays is coordinated with said pulse cycle in response to said electrocardiogram signal.

16. A method of measuring relative blood flow through at least a part of the body using penetrating radiation, comprising the steps of:
   a. passing from at least one source a first set of beams through a cross-sectional planar slice of the body at a first angle or first mean angle;
   b. passing a plurality of further sets of beam through said same cross-sectional planar slice at further angles or further mean angles, said further angles or further mean angles being different from said first angle or first mean angle and from each other;

c. each set of beams comprising a plurality of highly collimated individual beams, each said beam passing through said slice for a period of time at least equal to a pulse interval;

d. said plurality of beams in said sets of beams intersecting each other in said slice to define therein a two-dimensional matrix of elements, each element of said matrix being intersected by a plurality of beams;

e. deriving from each beam emerging from the body over the period of time at least equal to a pulse interval a number of momentary output signals, each said signal representing the momentary sum of the transmissions or absorptions of the elements of the body intersected by the beam;

f. determining from said momentary signals a difference signal representing the maximum difference between said momentary signals for each beam over said period of time;

g. deriving sets of discrete difference signals corresponding to the sets of beams, said difference signals being indicative of the transmission or absorption of blood flowing through each element of said matrix, the number of difference signals being sufficient to determine substantial discrimination between the transmission or absorption coefficients due to blood flow through neighboring elements of the matrix;

h. deriving from said difference signals resultant signals representing the transmissions or absorptions due to blood flow in the elements of said matrix; and i. producing in response to said resultant signals a representation of the transmissions or absorptions due to blood flow in said elements of the slice of the body.

17. A method as claimed in claim 16 wherein said beams in each set of beams are parallel.

18. A method as claimed in claim 17 wherein each set of beams is passed by linearly scanning said slice with said source, said source pausing to pass each beam in each set of beams for a period of time at least equal to a pulse interval.

19. A method as claimed in claim 18 wherein said further sets of beams are passed at said further angles by rotating said source about said plane in an arc at predetermined arc intervals.

20. A method as claimed in claim 19 wherein an electrocardiogram signal from the body is continuously monitored and the pausing and rotating of said source is coordinated with said pulse cycle in response to said electrocardiogram signal.

21. A method as claimed in claim 20 wherein each set of beams comprises 5 to 160 beams and wherein not more than 180 sets of beams are passed through each slice.

22. A method as claimed in claim 21 wherein each set of beams comprises 5 to 30 beams and wherein 60 to 90 sets of beams are passed through each slice.

23. A method as claimed in claim 16 wherein said beams in each set of beams continuously diverge from each other as they move further from said source.

24. A method as claimed in claim 23 wherein each set of beams is passed by linearly scanning said slice with said source, said source pausing to pass each beam in each set of beams for a period of time at least equal to a pulse interval.

25. A method as claimed in claim 24 wherein said further sets of beams are passed at said further mean angles by rotating said source about said plane in an arc at predetermined arc intervals.

26. A method as claimed in claim 25 wherein an electrocardiogram signal from the body is continuously monitored and the pausing and rotating of said source is coordinated with said pulse cycle in response to said electrocardiogram signal.

27. A method as claimed in claim 26 wherein each set of beams comprises 5 to 160 beams and wherein not more than 180 sets of beams are passed through each slice.

28. A method as claimed in claim 27 wherein each set of beams comprises 5 to 30 beams and wherein 60 to 90 sets of beams are passed through each slice.

29. A method of measuring relative blood flow through at least a part of the body using penetrating radiation, comprising the steps of:

passing, in sequence, each for a limited time duration, a plurality of sets of radiation beams, each set of beams comprising a plurality of highly collimated individual beams, through a cross-sectional planar slice of the body at different sequential angles or mean angles to define in said slice a two-dimensional matrix of elements each being intersected by a plurality of beams;

deriving from each beam emerging from the body a number of momentary output signals over said limited time duration, each said output signal representing the momentary sum of the transmissions or absorptions of the elements of the body intersected by the beam, and said number of momentary output signals including the maximum and minimum transmissions or absorptions of the elements of the body intersected by the beam during a pulsatile fluctuation of blood flow through said slice;

determining from said matrix signals a difference signal representing the difference between said maximum and minimum transmissions or absorptions for each beam and deriving sets of discrete difference signals indicative of the transmission or absorption of blood flowing through each element of said matrix, the number of difference signals being sufficient to determine substantial discrimination between the transmission or absorption coefficients due to blood flow through neighboring elements of the matrix; and producing in response to said difference signals a representation of the transmissions or absorptions due to blood flow in the slice of the body.

30. A method according to claim 29 wherein said limited time duration comprises at least a pulse interval.

* * * * *